(12) United States Patent
Castro et al.

(10) Patent No.: US 8,322,193 B2
(45) Date of Patent: Dec. 4, 2012

(54) TRANSDERMAL DIFFUSION CELL TESTING ARRANGEMENTS AND METHODS

(75) Inventors: Jose Castro, Garfield, NJ (US); Yu Sheng Zhang, Stewartsville, NJ (US); Luke Lee, Belle Mead, NJ (US)

(73) Assignee: Logan Instruments Corp., Somerset, NJ (US)

( * ) Notice: Subject to any disclaimer, the term of this patent is extended or adjusted under 35 U.S.C. 154(b) by 109 days.

(21) Appl. No.: 12/714,587

(22) Filed: Mar. 1, 2010

(65) Prior Publication Data
US 2011/0120215 A1 May 26, 2011

Related U.S. Application Data

(63) Continuation-in-part of application No. 12/623,763, filed on Nov. 23, 2009, now abandoned.

(51) Int. Cl.
*G01N 15/08* (2006.01)
(52) U.S. Cl. .......................... 73/38; 73/64.47; 73/64.56
(58) Field of Classification Search ........... 73/38, 64.47, 73/64.56
See application file for complete search history.

(56) References Cited

U.S. PATENT DOCUMENTS

| | | | | |
|---|---|---|---|---|
| 4,594,884 A | * | 6/1986 | Bondi et al. | 73/64.47 |
| 4,740,309 A | * | 4/1988 | Higuchi | 210/644 |
| 4,771,004 A | * | 9/1988 | Higuchi | 436/5 |
| 4,863,696 A | * | 9/1989 | Saydek et al. | 73/64.47 |
| 5,005,403 A | * | 4/1991 | Steudle et al. | 73/61.71 |
| 5,073,482 A | * | 12/1991 | Goldstein | 435/5 |
| 5,198,109 A | * | 3/1993 | Hanson et al. | 210/321.75 |
| 5,296,139 A | * | 3/1994 | Hanson et al. | 210/297 |
| 5,580,365 A | * | 12/1996 | Maiden | 65/104 |
| 5,659,130 A | * | 8/1997 | Chung et al. | 73/64.47 |
| 6,298,713 B1 | * | 10/2001 | Nandu et al. | 73/64.47 |
| 6,360,588 B1 | * | 3/2002 | Ross et al. | 73/38 |
| 6,821,419 B2 | * | 11/2004 | Hanson et al. | 210/297 |
| 7,470,535 B2 | * | 12/2008 | Yang et al. | 435/297.1 |

(Continued)

FOREIGN PATENT DOCUMENTS
JP 2007101283 A 4/2007

OTHER PUBLICATIONS

PermeGear Flow Type Franz Cells, available on the internet at <http://web.archive.org/web/20081121193739/http://www.permegear.com/franzflow.htm>, Nov. 21, 2008.*

(Continued)

*Primary Examiner* — David Rogers
(74) *Attorney, Agent, or Firm* — Brian Roffe

(57) ABSTRACT

Transdermal diffusion cell testing vessel includes a container defining a chamber having an opening against which skin is placed, and a casing arranged partially around and spaced apart from part of the container to define a compartment therebetween. The chamber retains a saline solution and is not in flow communication with the compartment through which water is circulated. The vessel includes separate inlet ports and outlet ports, each including a conduit communicating with the chamber or compartment. The outlet port of the chamber is angled downward relative to a horizontal upper surface of the container against which skin being tested is placed. The vessel is used for conducting transdermal diffusion cell testing in combination with a solution source fluidly coupled to each vessel, a waste receptacle fluidly coupled to each vessel, a syringe pump fluidly coupled to a respective vessel, and a sample collector fluidly coupled to the syringe pump(s).

20 Claims, 5 Drawing Sheets

U.S. PATENT DOCUMENTS

| | | | |
|---|---|---|---|
| 2003/0144626 A1* | 7/2003 | Hanson et al. | 604/73 |
| 2005/0019903 A1* | 1/2005 | Yang et al. | 435/288.2 |
| 2007/0089489 A1* | 4/2007 | Lewnard et al. | 73/38 |
| 2008/0233006 A1* | 9/2008 | Kennedy et al. | 422/68.1 |
| 2010/0071445 A1* | 3/2010 | Kamiyama et al. | 73/64.47 |

OTHER PUBLICATIONS

FDC-6 Transdermal Franz Cell System, available on the internet at <http://web.archive.org/web/20080208184533/http://www.kohan.com.tw/logan/902.html>, Feb. 8, 2008.*

Logan System 912SCT-S-1, available on the internet at <http://www.loganinstruments.com>, Oct. 2007.*

Performance evaluation of automated static Franz cell equipment for in vitro release and skin penetration testing A. Sieg, V. Caprasse, X. Thomas, S. Cornelis, V. Verhelst, undated.

Technology Showcase, Drug Delivery Technology, Jul./Aug. 2008, vol. 8, No. 7, p. 61, lower right hand corner.

Logan standard Bubble Free Cell sizes, from Logan Instruments Corp., undated.

Information Sheet about System 912 Automated Transdermal Diffusion Cell Sampling System: SYSTEM 912-24, Aug. 16, 2011.

Abstract of JP 2007101283(A), published Apr. 19, 2007.

* cited by examiner

FIG. 8
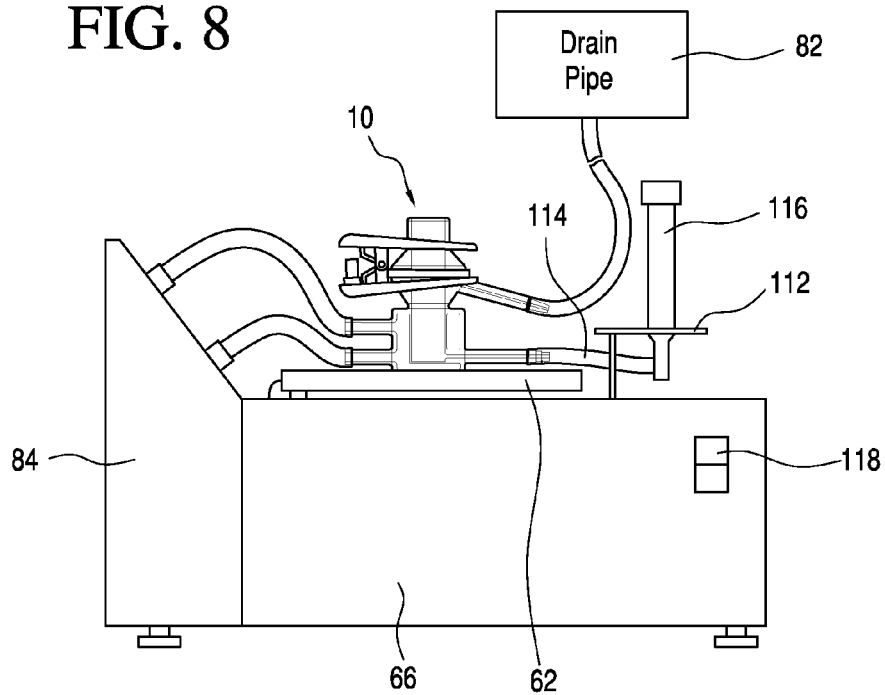
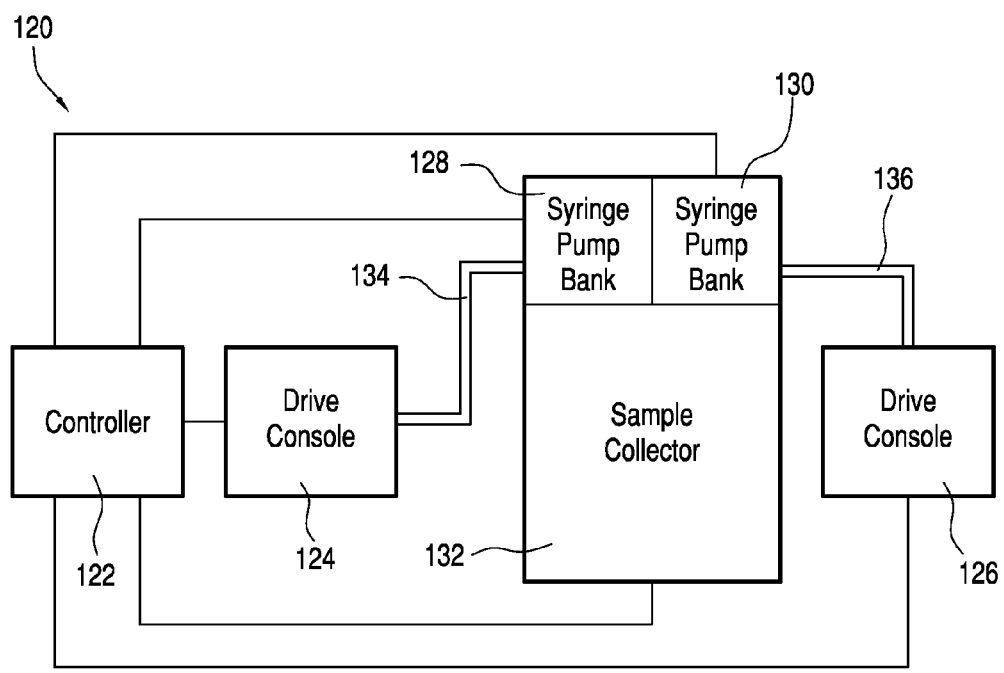
FIG. 9

TRANSDERMAL DIFFUSION CELL TESTING ARRANGEMENTS AND METHODS

CROSS REFERENCE TO RELATED APPLICATION

This application is a continuation-in-part of U.S. patent application Ser. No. 12/623,763 filed Nov. 23, 2009, incorporated by reference herein

FIELD OF THE INVENTION

The present invention relates generally to arrangements and methods for conducting transdermal diffusion cell testing. The present invention also relates to a method for introducing solution into an interior chamber of such a vessel when used for transdermal diffusion cell testing, either initially or to replenish solution removed during testing and/or sampling,

BACKGROUND OF THE INVENTION

Transdermal diffusion cell testing is a very tedious procedure. The primary objective of the test is to study the penetration rate of a pharmaceutical compound or drug through skin. A common way to perform transdermal diffusion cell testing is by mounting a layer of skin or epidermis between a cell cap (donor) and a cell body (receptor). The skin or epidermis is bathed from below with a solution, typically an isotonic saline solution, injected into a chamber in a vessel having an opening against which the skin or epidermis is placed through a port in the vessel.

The temperature of the saline bathing solution is usually maintained in a temperature range of about 32° C. to about 37° C. by a thermostatically controlled water flow that enters a lower port of a water jacket around the chamber in which the saline bathing solution flows, and circulates out of the water jacket through an upper port. Warm water is supplied and circulated by two (upper and lower) manifolds that are connected to a constant temperature bath.

A homogeneous distribution of the temperature of the saline bathing solution is sought to be accomplished by the agitating motion of a Teflon-covered magnetic stirring bar, driven by an external magnet and mounted on a timing motor.

The cell cap is open to the air, exposing the skin or epidermis to the ambient conditions of the laboratory environment. The open cap also allows for a finite dose application of study compounds to the skin or epidermis by use of a micropipette or stirring rod.

During the test, the pharmaceutical compound or drug penetrates the skin or epidermis slowly and dissolves in the saline bathing solution. A syringe is used to pull out or sample the saline bathing solution for further analysis. Such tests are typically performed in groups of three cells, with a view toward averaging the test results.

Improvements in the vessel used for transdermal diffusion cell testing are always being sought.

Objects and Summary of the Invention

A vessel for use in transdermal diffusion cell testing in accordance with the invention includes a container defining an interior chamber having an opening at an upper end, and a casing arranged at least partially around and spaced apart from at least a portion of the container to thereby define a compartment therebetween. The chamber will be operatively used to retain a saline bathing solution, or other solution for the transdermal diffusion cell test, and therefore is not in flow communication with the compartment through which a temperature-regulating fluid, such as water, is circulated.

The vessel also includes a first inlet port and a first outlet port spaced apart from one another and each including a conduit communicating with the chamber. The first outlet port is arranged above the first inlet port and proximate the opening at the upper end of the chamber. The first outlet port is angled downward relative to a horizontal upper surface of the container against which skin, epidermis or other material being tested is placed. The first inlet port is at or near a bottom of the container such that solution can be directed into the chamber from a bottom of the chamber and fills the chamber from the bottom to its top.

The angular inclination of the first outlet port is designed to ensure that a conduit within the first outlet port is at a highest point of the chamber when the vessel is tilted so that air bubbles that might form during introduction of solution into the chamber would naturally move toward the highest point in the conduit, and then move from there through a conduit connected to the first outlet port to a waste receptacle. In this manner, air bubbles are automatically removed from the chamber without requiring manual intervention. That is, the tilting of the vessel may be performed automatically by a tilting mechanism connected to a plate on which the vessel is placed, which in combination with the inclination of the first outlet port relative to the container, causes movement of any air bubbles to the first outlet port and thus would not remain under the skin and adversely affect the diffusion of the pharmaceutical compound or drug through the skin into the solution. Tilting of the vessel may be performed prior to and/or simultaneously with introduction of solution into the chamber.

With the foregoing structure, the present invention significantly improves transdermal diffusion cell testing by eliminating the presence of air bubbles between the skin and the solution and thereby improving the testing results. Moreover, by maintaining the temperature of the solution in multiple vessels in a fixed range, a subsequent averaging of the test results from the vessels provides more accurate test results since variability in the temperature conditions of multiple vessels has been eliminated.

A method for introducing solution into an interior chamber of such a vessel including connecting a fill tube from a syringe pump to the first inlet port of the vessel, connecting the syringe pump to a solution source, orienting the syringe pump such that a syringe of the syringe pump has its inlet facing downward and its plunger vertically movable upward and downward, and controlling the syringe pump via a controller such that solution is drawn from the solution source through the syringe to the chamber in the vessel. In this manner, air bubbles in the solution drawn from the solution source enter into a chamber of the syringe and are thus prevented from entering into the chamber.

Variations and enhancements of this method are possible and include controlling the syringe pump to draw solution from the solution source and pass it to the chamber until the solution exits the chamber into the first outlet port, placing the vessel on a plate and while the syringe pump is controlled to pass solution into the chamber, tilting the plate to cause tilting of the vessel until a highest point of the chamber is situated in the conduit of the first outlet port such that any air bubbles against the skin enter into the conduit of the first outlet port. Additionally, a purge tube may be connected to the first outlet port of the vessel and the syringe pump controlled to pass solution into the chamber in the vessel until the solution exits the chamber into the first outlet port and flows into the purge tube. If the purge tube is connected to a drain pipe, the syringe may be controlled to pass solution into the chamber in the vessel until the solution exits the chamber into the first outlet port, flows into the purge tube and flows into the drain pipe.

An arrangement for conducting transdermal diffusion cell testing using the vessel described above includes a solution source fluidly coupled to each vessel, a waste receptacle fluidly coupled to each vessel, a syringe pump fluidly coupled to a respective vessel, and a sample collector fluidly coupled to the syringe pump(s). Each syringe pump is controlled to provide a first flow path of solution from the solution source to the waste receptacle through the associated vessel in order to fill the chamber with solution and to provide a second flow path of solution from the chamber to the sample collector.

Another arrangement for conducting transdermal diffusion cell testing using the vessels described above includes a plate arranged to receive or retain at least one vessel, a tilting mechanism coupled to the plate and arranged to tilt the plate, a fluid circulating mechanism that circulates a temperature-regulating fluid through the compartment via the second inlet and outlet ports, a sampling manifold including at least one sampling port, a respective sampling line connecting the first inlet port of a respective vessel to a respective sampling port on the sampling manifold, and at least one syringe insertable into the sampling manifold to enable sampling of solution in a respective vessel. The sampling manifold may be mounted onto the tilting mechanism.

Yet another arrangement for conducting automated transdermal diffusion cell testing using the vessels described above includes a controller, at least one drive console, each including a tilting mechanism that tilts the vessels and a fluid supply mechanism that supplies a regulating fluid to the compartment of each vessel, a sample collector, and at least one syringe pump assembly. Each syringe pump assembly including a plurality of syringes oriented with a plunger facing upward and an outlet downward, a structure for retaining the syringes, a mechanism for moving the plunger of each syringe in a controlled manner, and ports to enable connections of fluid conduits to the vessels to allow for flow of solution to and from the chambers in the vessels and to the sample collector. The controller controls each drive console, the sample collector and each syringe pump assembly to control flow of samples of solution from the vessels to the sample collector through the syringe pump assembly.

Other and further objects, advantages and features of the present invention will be understood by reference to the following specification in conjunction with the annexed drawings.

BRIEF DESCRIPTION OF THE DRAWINGS

The invention, together with further objects and advantages thereof, may best be understood by reference to the following description taken in conjunction with the accompanying drawings wherein like reference numerals identify like elements.

FIG. 8 is a side view of an arrangement in accordance with the invention including a sampling manifold.

FIG. 9 is a schematic of a complete arrangement in accordance with the invention for transdermal diffusion cell testing.

DETAILED DESCRIPTION OF THE INVENTION

Figure 1:
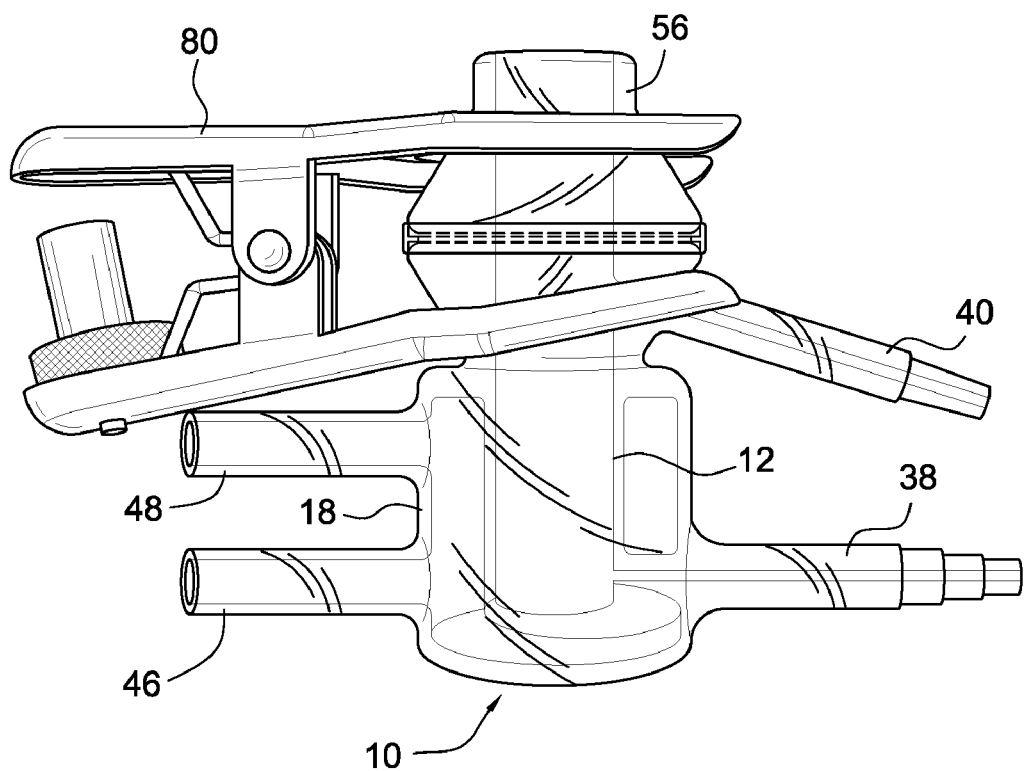
FIG. 1 is a perspective view of a vessel in accordance with the invention.

Referring to the accompanying drawings wherein like reference numerals refer to the same or similar elements, FIG. 1 is a perspective view of a vessel in accordance with the invention that is designated generally as 10. Vessel 10 includes a container 12 defining an interior chamber 14 having an opening 16 at an upper end and a casing 18 arranged at least partially around and spaced apart from at least a portion of the container 12. As such, a compartment 20 is defined between the container 12 and casing 18 and is entirely separate from the chamber 14, i.e., there is no flow communication between the chamber 14 and the compartment 20. The container 12 and casing 18 are integral with one another, and may be formed from a common material, such as glass or plastic.

The container 12 includes a substantially tubular side wall 22 and a bottom wall 24 and the casing 18 includes a substantially tubular side wall 26 surrounding part of the side wall 22 of the container 12 and a bottom wall 28 underneath the bottom wall 24 of the container 12. In this manner, the compartment 20 is defined between the side walls 22, 26 of the container 12 and casing 18 and between the bottom walls 24, 28 of the container 12 and the casing 18. Compartment 20 also surrounds the side wall 22 of the container 12 and thus, in operation when a fluid is circulated through the compartment 20, enables regulation of the temperature of a solution in the chamber 14 of the container 12.

Alternatively, the side walls 22, 26 may have other than tubular forms. Moreover, the side walls 22, 26 and bottom walls 24, 28 may be substituted for by any construction of one or more walls which define two chambers separate from one another yet enabling heat transfer therebetween and with one of the chambers, most likely the innermost chamber, has an opening against which skin, epidermis or other material whose diffusion is being tested, is placed.

Figure 2:
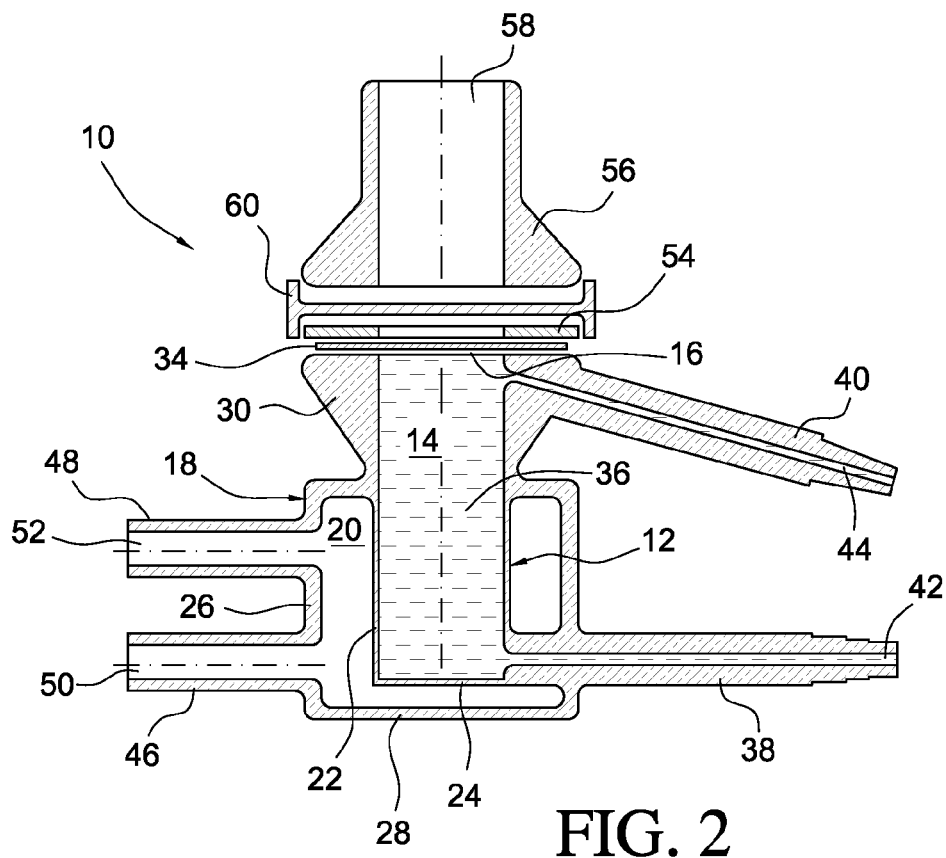
FIG. 2 is a cross-sectional view of the vessel shown in FIG. 1 when in an untilted use state for testing and sampling.

The container 12 includes a flanged upper end region 30 defining a horizontal upper surface 32 against which skin 34, or another material for which diffusion testing is being performed, is placed during use of the vessel 10. An opening 16 is provided in the upper surface 32 to enable contact between a solution in the chamber 14 and the skin 34. In this manner, a pharmaceutical compound or drug is diffused through the skin 34 or other material into the solution 36 in chamber 14. The upper end region 30 of the container has a variable thickness, as shown in FIG. 2.

The casing 18 extends around only a lower part of the container 12.

Vessel 10 also includes a first, solution inlet port 38 near or at a bottom of the side wall 22, and a first, solution outlet port 40 near or at a top of the side wall 22. The first, solution outlet port 40 may also be referred to as a purge tube. The first, solution inlet and outlet ports 38, 40 are spaced apart from one another and each includes a conduit 42, 44, respectively, communicating with the chamber 14. The first, solution outlet port 40 is thus arranged above the first, solution inlet port 38 and also, proximate the opening 16 at the upper end region 30 of the container 12. A saline bathing solution 36, or comparable solution, is operatively situated in the chamber 14, i.e., it is initially directed into an empty chamber 14 through the first, solution inlet port 38 with excess being removed through the first, solution outlet port 40. Replacement or replenishment solution 36 is also directed into the chamber 14 through the first, solution inlet port 38.

The first, solution inlet port 38 extends through the side wall 26 of the casing 18 to connect to the side wall 22 of the container 12. This enables the conduit 42 to communicate with the chamber 14 without communicating with the compartment 20. Also, the first, solution inlet port 38 is substantially horizontal when the vessel 10 rests on or is supported by a horizontal surface.

The first, solution outlet port 40 is angled downward relative to the horizontal upper surface 32 of the container 12. The acute angle is variable and may be in a range from about 20° to about 30° relative to the horizontal upper surface 32 of the container 12. Other angles and angle ranges can be provided in accordance with the invention without deviating from the scope and spirit thereof and are contemplated to be within the inventor's possession. Since the casing 18 extends around only a lower part of the container 12, the first, solution outlet port 40 is connected directly to the side wall 22 of the container 12 at a location where the casing 18 is not present.

Vessel 10 also a second fluid inlet port 46 near or at a bottom of the side wall 26, and a second fluid outlet port 48 near or at a top of the side wall 26, and thus above the second fluid inlet port 46. The second fluid inlet and outlet ports 46, 48 are spaced apart from one another and each includes a conduit 50, 52, respectively, communicating with the compartment 20. Also, the second fluid inlet and outlet ports 46, 48 are substantially horizontal when the vessel 10 rests on or is supported by a horizontal surface.

With the foregoing structure, there are two fluid paths in the vessel 10. A first fluid path for solution 36 is defined by the conduit 42 in the first, solution inlet port 38, the chamber 14 and the conduit 44 in the first, solution outlet port 40, while a second fluid path for water or other temperature-regulating fluid is defined by the conduit 50 in the second fluid inlet port 46, the compartment 20 and the conduit 52 in the second fluid outlet port 48.

As mentioned above, water may be directed on the second fluid path to regulate the temperature of the solution 36 in the chamber 14. To this end, the water may be continuously flowing or circulating through the compartment 20 to maintain the temperature of the solution 36 in the chamber 14 at a substantially constant temperature or within a predetermined temperature range. The manner in which temperature of the solution 36 in chamber 14 is regulated by the flow of water through the compartment 20 surrounding the chamber 14 is known to those skilled in the art, and is based on principles of heat transfer through the tubular side wall 22 of the container 12.

As shown in FIG. 2, in use, the vessel 10 may be used in conjunction with a ring 54 that is placed against the upper surface of the skin 34 and holds the skin 34 to the upper surface 32 of the vessel 10. An upper cap 56 may be placed against the ring 54 and has a channel 58 aligning with the opening 16 such that the skin 34 may be exposed to the ambient conditions of the laboratory environment. When desired, exposure of the skin 34 to the ambient environment is prevented by placing a seal cap 60 with a flange over the ring 54. A clamp or similar holding mechanism 80 may be provided to retain the upper cap 56 and/or seal cap 60 in secure engagement with the vessel 10.

The dimensions of the vessel 10 may vary depending on the situation in which the vessel 10 may be use. In one embodiment, the diameter of the interior surface of the side wall 22 defining the chamber 14, the inner diameter of the ring 54 and the diameter of the channel 58 are substantially the same. The diameter of the channel 58 may be about 0.60 inches or about 15.2 mm. The ring 54 may have an inner diameter of about 15.1 mm and a thickness of about 1.6 mm Vessel 10 may be used in any number of different testing systems and apparatus, and is not necessarily limited to testing skin and other similar materials to analyze the diffusion of a material through the skin or other material. Of course, transdermal diffusion cell testing is a preferred use of the vessel 10.

By providing the vessel 10 with the angled first, solution outlet port, an important advantage can be achieved when filling solution into the vessel in conjunction with transdermal diffusion cell testing, as well as when replacing solution removed from the vessel for testing and sampling purposes. Specifically, the vessel 10 may be mounted to a tilting system (described below) that tilts the vessel 10 with a view toward eliminating any bubbles that might be present under the skin 34 as a result of the solution filling or replacement operations.

A major problem with transdermal diffusion testing is the presence of air bubbles under the skin, i.e., air bubbles forming spaces between the skin and solution in a solution chamber of the vessel used in the diffusion cell testing. Since diffusion testing relies on contact between the skin and the solution to enable penetration of the pharmaceutical compound or drug from the skin into the solution, the bubbles prevent complete diffusion over the entire surface of the skin and thus result of the testing, the particular effect being indeterminate as it is dependent on the amount and size of the bubbles. It is therefore possible that when a large number and/or large size of bubbles is/are present, there is no penetration of the pharmaceutical compound or drug into the solution, or only very limited penetration.

A common, conventional technique to remove bubbles under the skin is to rotate the vessel used in the diffusion cell testing to move the bubbles away from the skin or alternatively, to insert a tube into the solution to vacuum the air bubbles away from the skin. Both of these are manuals tasks that are very tedious. Moreover, after removing the bubbles, the test technician must add more solution into the solution chamber in the vessel to ensure that there is 100% contact of the skin with the solution. However, due to variations in the size and/or the amount of the bubbles, the replacement solution cannot be controlled. An unavoidable consequence of these bubble removal techniques is that each vessel, of a plurality of vessels being used to determine the diffusion rate of the same pharmaceutical compound or drug to enable averaging of the results, have different diffusion rates and create different test results from each vessel.

Yet another disadvantage of the required manual removal of bubbles from between the skin and the solution is that diffusion cell tests could run as long as seven days, and the sampling interval to remove solution for analysis could be as short as every two hours. This means that the test technician has to practically sleep next to the test equipment and wake up every two hours to take samples from the vessels, replace the removed solution, and if necessary, manually eliminate any bubbles and then add more replacement solution.

Figure 4:
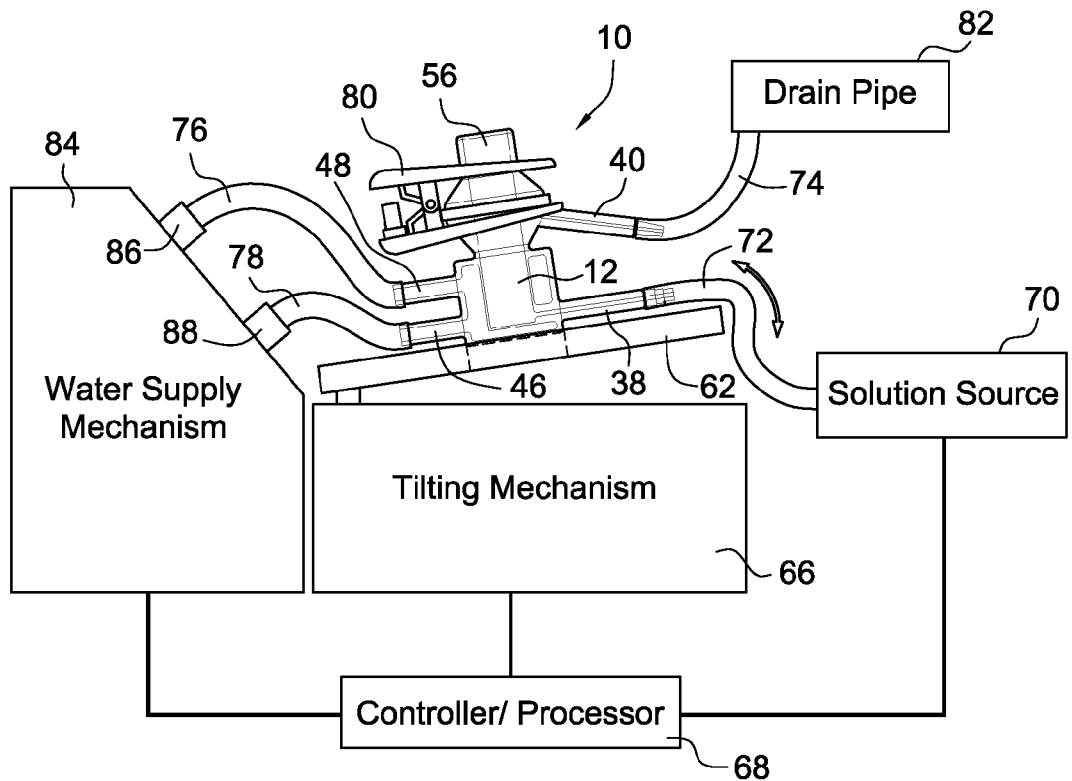
FIG. 4 is a schematic showing a vessel of FIG. 1 with its connection to enable transdermal diffusion cell testing.
Figure 5:
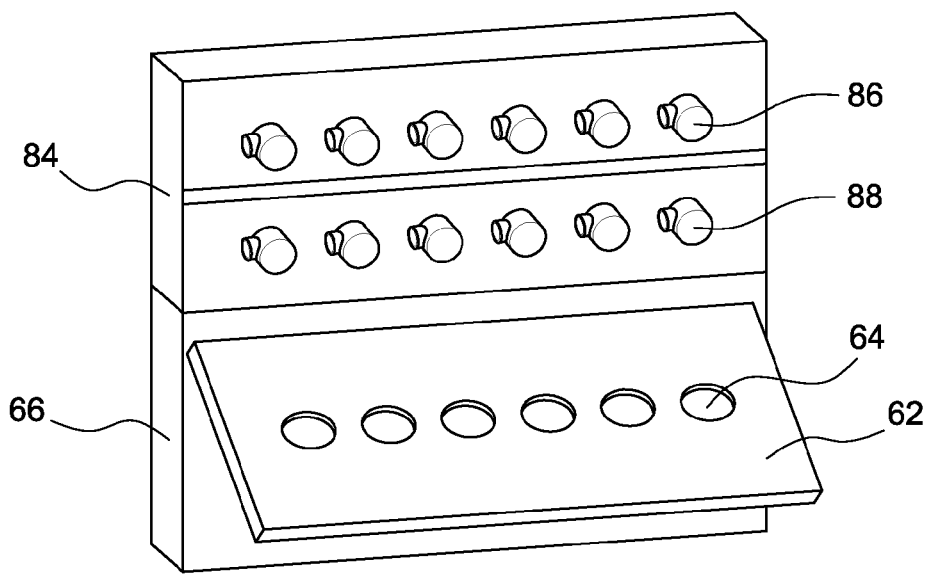
FIG. 5 is a schematic top view showing a tilting mechanism and water supply mechanism for use with a plurality of vessels of FIG. 1.

Using vessel 10 in accordance with the invention enables a practically guaranteed manner to eliminate any bubbles under the skin 34 during testing of the skin 34. Specifically, with reference to FIGS. 4 and 5, the vessel 10 is placed onto a receiving plate 62 that has apertures 64 for receiving a plurality of vessels 10 and a tilting mechanism 66 is connected to the plate 62 to tilt the plate 62, and thus all of the vessel 10 placed thereon. As shown in FIG. 5, the plate 62 has six apertures 64. However, the number of apertures in the plate 62 may vary and not all of the apertures have to receive vessels 10 in order to enable operation of the tilting mechanism 66. The combination of the plate 62 with apertures 64 thereon or therein and the tilting mechanism 66 may be considered to be a tilting device.

Tilting of the plate 62 by the tilting mechanism 66 may entail elevating one end of the plate 62 relative to or more than the other end of the plate 62 to thereby change the orientation of the plate 62 from a substantially horizontal plane to an angled plane. The tilting mechanism 66 can tilt the plate 62 to any one of a plurality of different angular positions, e.g., an angle of 30° relative to the horizontal. The tilting mechanism 66 may generally include a housing, a motor arranged therein, a processor or controller arranged therein and an actuator that converts action from the motor, i.e., rotary action, into a tilting movement of the plate 62 that is positioned above the housing as shown in FIGS. 4 and 5. Thus, the processor issues commands to the motor or its controller to cause the actuator to tilt the plate 62, either to a tilted position when solution is introduced and formation of bubbles under the skin 34 is sought to be prevented, or to a horizontal position after solution is in the chamber 14 and it is now desired to conduct the testing and/or sampling.

The tilting device may be an instrument manufactured by the current assignee, Logan Instruments Corp. of Somerset, N.J. and designated the FDC-6T, a vertical cell drive console with tilting device.

The purpose of the tilting of the vessels 10 via the tilting mechanism 66 is to provide that the highest point of the chamber 14 is within the conduit 44 defined by the first, solution outlet port 40. This situation should arise at least at the end of the tilting operation. In one embodiment, the vessels 10 are tilted prior to introduction of the solution into the chamber 14 and solution is introduced into the chamber 14 only after the highest point of the chamber 14 is within the conduit 44. Alternatively, the tilting may begin after solution has already entered the chamber 14. Regardless of the order in which the tilting of the plate 62 and filling or replenishment of solution into the chamber 14 is performed (and which may also be performed simultaneously), the tilting should be coordinated with the solution filling such that the solution does not enter into the inlet of the conduit 44 until the chamber 14 is otherwise completely full of solution. This coordination may be performed by a controller or processor 68 that controls the tilting mechanism 66 and a solution supply mechanism 70, e.g., the pumps that supply solution from a common solution source to fill tubes 72 coupled to the first, solution inlet ports 38.

Figure 3:
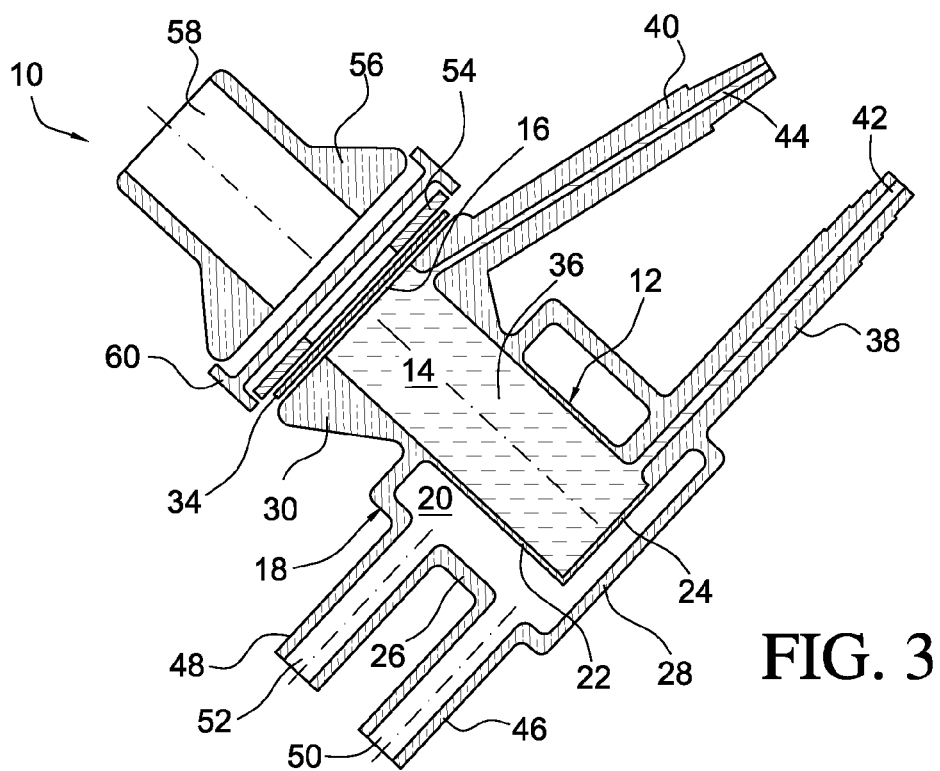
FIG. 3 is a cross-sectional view of the vessel shown in FIG. 1 when in a tilted state in which solution is introduced into a chamber therein.

In an exemplifying use to fill solution into the chamber 14, in a preliminary stage, the vessels 10 are placed into the receiving apertures 64 of the plate 62 and fill tubes 72 are connected from a solution source associated with the solution supply mechanism 70 to the first, solution inlet port 38 of each vessel 10. The tilting mechanism 66 is activated by the processor 68 to tilt the plate 62 and thus the vessels 10 in the apertures 64 thereon until the highest point of the chamber 14 is within the conduit 44 of the first, solution outlet port 40 (the position of the vessel 10 shown in FIG. 3). Solution may then be directed into the solution chamber 14 of each vessel 10 through the first, solution inlet port 38 at the bottom of the solution chamber 14, and the solution gradually rises until it comes into contact with the skin 34. As noted above, solution may start to be introduced into the chamber 14 before the tilting operation is complete.

The direction of tilt depends on the side to which the first, solution outlet port 40 is placed and in the illustrated embodiment, the tilting mechanism 66 tilts the plate 62 counterclockwise. The degree of tilt also depends on the construction of the vessels 10. The overall objective of the tilting of the vessels 10 is to cause air bubbles that might form under the skin 34 as a result of the chamber filling operation to move out of contact with the skin 34 to ensure a complete contact between the skin 34 and the solution in chamber 14. Therefore, the invention applies the inherent property of air as being lighter than the solution so that the air bubbles will move to the highest point of the solution chamber 14 which will eventually be within the conduit 44 in the first, solution outlet port 40. Further, any air bubbles will then travel through the conduit 44 within the first, solution outlet port 40 to a purge tube 74 connected to the first, solution outlet port 40, which purge tube leads to a drain pipe 82 or other form of waste receptacle that may collect waste from all of the vessels 10. Continued introduction of solution into the chamber 14 through the first, solution inlet port 38 after the highest point of the chamber 14 is within the conduit 44 will then causes the air bubbles in the conduit to be purged therefrom and forced into the purge tube 74 to the drain pipe 82.

After the solution has been filled into the chambers 14 of the vessels 10, the tilting mechanism 66 is again activated to restore the plate 62 to a horizontal plane because the testing and sampling is performed while the vessels 10 are in their horizontal, untilted state. Thus, the tilting mechanism 66 is preferably activated to tilt the plate 62 and vessels 10 thereon for the initial filling of solution into the chambers 14 as well as for replacement of solution into the chambers 14 (which is necessary after testing and sampling that require removal of solution from the chamber 14).

The foregoing technique for tilting the vessels 10 therefore automates the air bubble removal process and eliminates the need for testing personnel to manually rotate vessels or insert a tube into the solution chambers of vessels to remove air bubbles that might form during the initial filling of solution into the solution chambers or replacement of solution after testing and sampling.

To summarize, a method for introducing solution into the interior chamber of the vessel 10 includes preparing the vessel 10 for the transdermal diffusion cell testing by placing skin 34 over the opening 16 on the upper horizontal surface 32 of the vessel 10, and securing the skin 34 in this position, e.g., using a ring 54 and clamp (not shown). The method also entails placing the vessel 10 on the plate 62, e.g., into apertures 64 on the plate 62, connecting a respective fill tube 72 to the first, solution inlet port 38 of the vessel 10, and connecting the fill tube 72 to a solution supply mechanism 70. These steps may be performed in any order. Then, the method entails directing solution from the solution supply mechanism 70 through the first, solution inlet port 38 into the chamber 14 in the vessel 10 until the solution exits the chamber 14 into the first, solution outlet port 40, and tilting the plate 62 to cause tilting of the vessel 10 until a highest point of the chamber 14 is situated in the conduit 44 of the first, solution outlet port 40 such that any air bubbles against the skin 34 enter into the conduit 44 of the first, solution outlet port 40. Note that to practice this method, a vessel other than vessel 10 may be used, e.g., one that does not include the casing 18 and provides other means to regulate the temperature of the solution in the chamber 14. Vessel 10 though is a preferred vessel for use in this method.

In one embodiment, a respective purge tube 74 is connected to the first, solution outlet port 40 of the vessel, in which case, the solution is directed from the supply mechanism 70, while the vessel 10 has been or is being tilted, through the first, solution inlet port 38 into the chamber 14 in the vessel 10 until the solution exits the chamber 14 into the first, solution outlet port 40 and flows into the purge tube 74. The purge tube 74 connects to a drain pipe 82 or waste receptacle at its opposite end, so that the excess solution may continue to flow into the drain pipe 82. A sufficient amount of solution may be directed through the chamber 14 when filling it to prevent a backward flow of air from the purge tube 74 or the purge tube 74 may be designed to prevent the backward flow of air to the chamber 14. This may also be achieved through appropriate design of the angled nature of the first, solution outlet port 40, and/or via appropriate fluid connections of the purge tube 74 to the drain pipe.

The method for introducing solution in the chamber 14 encompasses both the initial filling of the chamber 14 with solution was well as the replacement or replenishment of solution after testing and sampling that involve removal of solution from the chamber 14.

The vessel 10 may also be used in a transdermal diffusion cell testing procedure wherein a plurality of such vessels are used and it is desired to maintain a substantially uniform temperature distribution in all of the vessels, i.e., maintaining substantially the same, or an even or stable, temperature of the solution in the solution chambers 14 of the vessels 10. This method entails after coupling the vessels 10 to the solution circulation systems described above, providing a manifold in a water supply mechanism 84 with a plurality of fluid outlets 86, connecting a respective fill tube 76 from each fluid outlet 86 to the second, fluid inlet port 46 of each vessel, connecting a respective drain tube 78 from the second, fluid outlet port 48 of each vessel 10 to a respective fluid inlet 88 of the water supply mechanism 84, and directing fluid from a common receptacle in the water supply mechanism 84 into the compartments 20 in the vessels 10 through the fluid outlets 86, the fill tubes 76 and the second, fluid inlet ports 46 to fill the compartments 20, with excess fluid being removed through the second, fluid outlet ports 48 into the drain tubes 78 and through the fluid inlets 88. Each fluid outlet and inlet 86, 88 may be provided with a shut-off valve (not shown).

The water supply mechanism 84 may also heat the water and thus may be a water heater circulator, such as an instrument designated the VTC-200 manufactured by the current assignee Logan Instruments Corp., of Somerset, N.J., The water supply mechanism 84 is coupled to the controller or processor 68 and controlled to circulate water through the compartments 20 in the vessels 10 mounted on the plate 62 during the testing stage.

Fluid may be directed from the common receptacle in the water supply mechanism 84 into the compartments 20 in the vessels 10 by pumping the fluid into the compartments 20. Such a pumping system may be internal to the water supply mechanism 84.

One of the features of the vessel 10 is that the second, fluid inlet port 46 may be arranged at or near a bottom of the compartment 20 and the second, fluid outlet port 48 may be arranged at or near a top of the compartment 20 and above the second, fluid inlet port 46 such that the compartments 20 in the vessels 10 are filled from the bottom to their top.

A computer program is created to be used by the processor in order to coordinate and manage the transdermal diffusion cell testing procedure using a vessel in accordance with the invention. The program is arranged to control the pumps, valves and other components that control the amount of solution in the chambers 14 (the solution supply mechanism 70), the tilting mechanism 66 that tilts the plate 62, the pumps, valves and other components that heat and circulate water through the compartments 20 (the water supply mechanism 84), as well as the sampling and testing apparatus (not shown). The controller may be an automated system controller manufactured by the current assignee, Logan Instruments Corp. of Somerset, N.J., and designated the ASC-100. Additional details about this controller are provided below with reference to FIG. 9.

Figure 7:
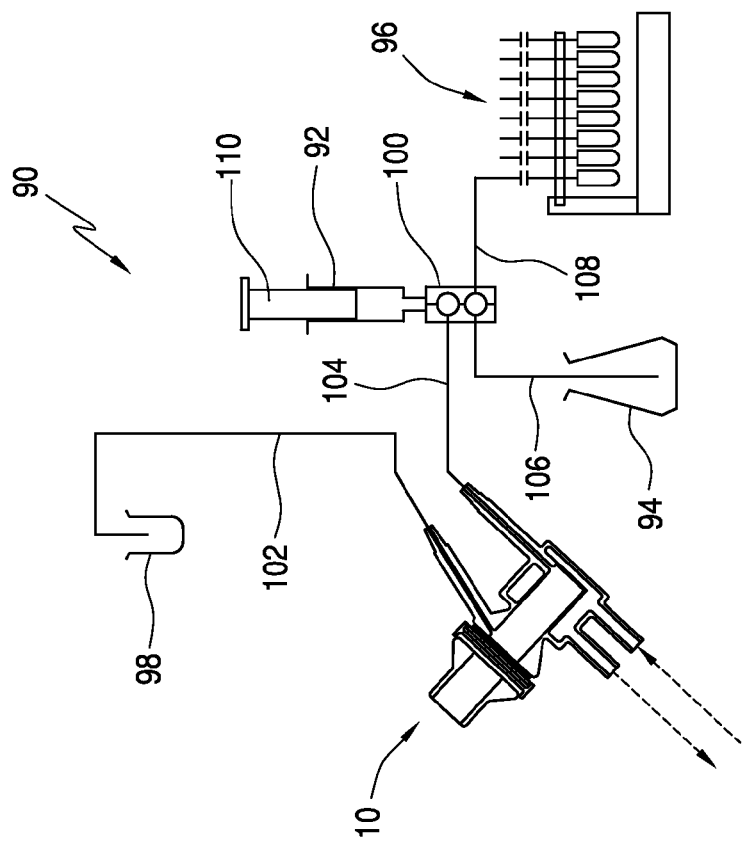
FIG. 7 is a schematic showing the manner in which the vessel of FIG. 1 is used in a transdermal diffusion test.
Figure 6:
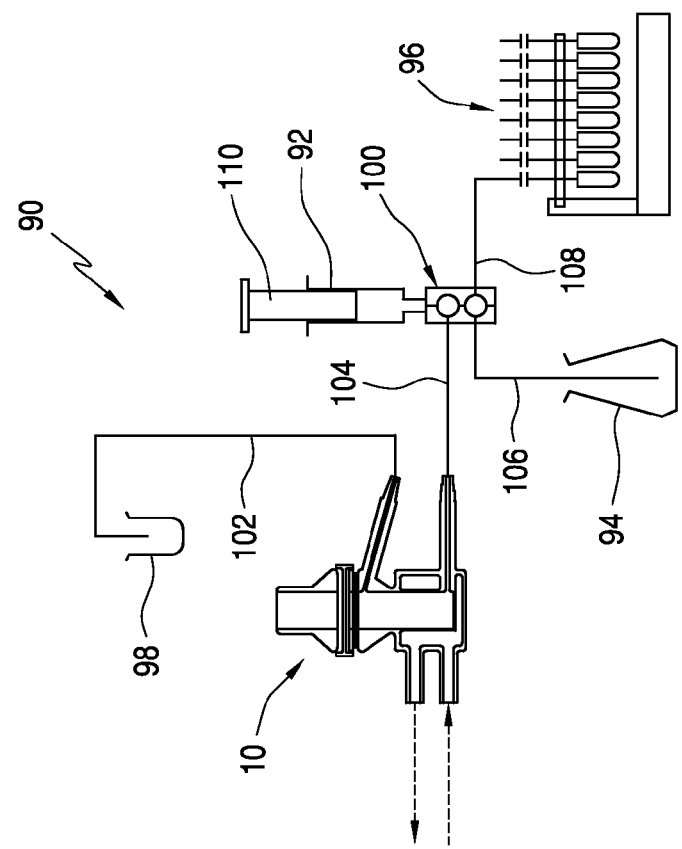
FIG. 6 is a schematic showing the manner in which the vessel of FIG. 1 is used in a transdermal diffusion test.

Referring now to FIGS. 6 and 7, an arrangement 90 is shown wherein each vessel 10 is used with a respective syringe pump 92, a respective or common media replacement container 94 which may equivalent to the solution source 70, a common sample collector 96, a respective or common waste receptacle 98, which may be equivalent to the purge tube 74 and/or drain pipe 82, and a respective fluid coupling block 100 associated with the respective syringe pump 92 in a manner known to those skilled in the art. A fluid conduit 102 connects the vessel 10 and the waste receptacle 98, a fluid conduit 104 connects the vessel 10 and the fluid coupling block 100, a fluid conduit 106 connects the media replacement container 94 and the fluid coupling block 100, and a fluid conduit 108 connects the sample collector 96 and the fluid coupling block 100. The set-up of fluid conduits is repeated for each vessel 10. The fluid coupling block 100 may be considered separate from or part of the syringe pump 92.

In this arrangement 90, the water supply mechanism 84 that supplies water to regulate the temperature of the solution and the mechanism 66 that tilts the plate 62 on which the vessels 10 are arranged are not shown but are present and function as described above.

FIG. 6 shows a condition in which a controller 68 runs a computer program embodied on computer-readable media that conducts sampling of the media in the vessel(s) 10 on the plate 62. In this condition, each vessel 10 is in an untilted state, which is the same state it is in during the test.

When it is time the perform the sampling, the controller 68 controls the syringe pump 92 to take samples from each vessel 10 through fluid conduit 104 a short time before the sampling time, e.g., a few minutes, to perform an optional but preferred pre-conditioning of the syringes 110 of the syringe pump 92 and then takes samples at the sampling time. Other times for the optional pre-conditioning of the syringes 110 may also be selected. The arrangement 90 may be controlled to waste a small quantity of media, e.g., 0.5 ml, to wash the sample delivery line, conduit 108, and then after the washing is concluded, initiate the delivery of the sample into an HPLC vial of the sample collector 96. Thereafter, the syringe pump 92 is controlled to draw all remaining media from the delivery line 108 and send it back to the vessel 10 through fluid conduit 104.

FIG. 7 shows a condition in which a controller runs a computer program that refills media into each vessel 10 to replace media removed during sampling. The controller 68 controls the syringe pump 92 to draw replacement media from the replacement media container 94 and force it into the vessel 10.

An important aspect of this arrangement is that the syringe 110 of the syringe pump 92 is oriented to be pulled in an upward direction with an inlet of the syringe 110 thereby facing downward. As such, air bubbles that may be in the media, e.g., entrained in the media during its flow from the media replacement container 94 to be passed into the vessel 10, are retained in a chamber in the syringe 110 and do not flow through to the vessel 10. Thus, any air bubbles would disappear in the syringe chamber and be purged out of the system. By using the syringe pump 92 to transfer media from the media replacement container 94 to the vessel 10 via the syringe pump 92 and the unique orientation of the syringe 110 thereof in the upward direction, i.e., with its plunger vertically oriented above its outlet, an additional step to prevent the presence of air bubbles underneath the skin 34, and thereby improve the transdermal diffusion test results, is provided.

FIG. 8 is a side view of an arrangement in accordance with the invention which includes the tilting mechanism 66, water supply mechanism 84, one or more vessels 10 and remaining structure shown in FIG. 4, unless otherwise stated. In addition, in this embodiment, there is a sampling manifold 112 mounted or otherwise arranged on the tilting mechanism 66, or other part of the drive console that includes the tilting mechanism 66 and water supply mechanism 84. The sampling manifold 112 is preferably arranged on a portion of the tilting mechanism 66 that does not tilt, i.e., that is not tilted when the plate 62 is tilted.

The sampling manifold 112 is designed to allow users to obtain samples of the solution from chamber 14 while the vessels 10 are maintained on the tilting mechanism 66, i.e., avoiding the need in prior art arrangements of removing the vessels in order to conduct sampling of the solution therein. More specifically, the vessels 10 may be continually arranged on the plate 62 without requiring removal therefrom to perform the sampling operation.

A sampling line 114 is connected at one end to the lower port of the solution chamber 14 and at the other end mounted to a sampling port on the sampling manifold 112. A syringe 116 is inserted into connection with the sampling manifold 112, e.g., into the sampling port, to perform the sampling from the vessels 10. The sampling manifold 112 may be elevated above the upper surface of the tilting mechanism 66 to allow for space for fluid conduits to extend from a bottom of the sampling ports.

The sampling manifold 112 may include a plurality of sampling ports, e.g., one for each vessel 10 on the plate 62. Filters, not shown, may be placed on the sampling manifold 112 to filtrate the samples.

As mentioned above, sampling of the solution is performed while the vessels 10 are in an untilted state, i.e., in a flat position. However, solution replacement is conducted while the vessels 10 are tilted, e.g., to an angle of 30° to the horizontal, and to this end, a button 118 may be actuated to cause tilting of the plate 62 and the vessels 10 received thereon. The length of the sampling lines 114 is selected to enable the tilting movement of the vessels 10 on the plate 62 while maintaining the connection between the lower port of the solution chamber 14 of the vessels 10 and the sampling port of the sampling manifold 112.

Referring now to FIG. 9, a schematic of an arrangement 120 in accordance with the invention is shown which includes a controller 122 (which may be the same as or encompass controller/processor 68), first and second drive consoles 124, 126, first and second syringe pump assemblies 128, 130 and a sample collector 132. This entire arrangement 120 constitutes an automated transdermal diffusion cell sampling system. Moreover, the arrangement 120 enables automation of the entire diffusion cell testing process using a plurality of vessels 10, while eliminating the problem of bubbles forming in the vessels against the skin, ensuring an even temperature of the solution being used to conduct the diffusion cell testing, taking samples from the solution when necessary or desired and replacing solution back into the solution chambers after sampling resulting in removal of solution therefrom.

Each drive console 124, 126 includes a tilting mechanism, water supply mechanism, and when the vessels are placed onto the plate of the tilting mechanism, the necessary fluid connections between the water supply mechanism and the vessels. Each syringe pump assembly 128, 130 includes a plurality of syringe pumps, all oriented with their plunger facing upward and outlet downward. The number of syringe pumps in the syringe pump assemblies 128, 130 may be equal to the number of vessels on the plate of the tilting mechanism of the drive console 124, 126.

Each syringe pump assembly 128, 130 includes a structure for retaining a plurality of syringes and a mechanism for moving the plunger of each syringe in a controlled manner. Each syringe pump assembly 128, 130 also includes ports to enable connections of fluid conduits necessary to allow for flow of the solution to and from the solution chambers in the vessels 10 and to sample collector 132.

The sample collector 132 may be a sample collector sold by Logan Instruments Corp. designated SCT-160V. This sample collector includes two sample racks, a lower sample rack with an array of receptacles that are designed to receive, for example, glass sample tubes, and an upper sample rack with an array of receptacles that are designed to receive, for example, HPLC vial sample tubes to enable the samples to be collected into sealed HPLC vials. The upper sample rack may be placed on top of the lower sample rack. As such, users can easily switch the trays for whatever test is being conducted.

The sample collector 132 may include a recycle system, not shown, that allows the samples to be returned to the cells. The delivery manifold may be changed so that it can be used as a single channel delivery system up to a 48 channel delivery system. A piercing mechanism, not shown, may be provided on the sample collector 132 to enable to pierce HPLC vials.

The controller 122 may be directly or indirectly connected to the first and second drive consoles 124, 126, the first and second syringe pump assemblies 128, 130 and the sample collector 132 to control electrical, electromechanical or mechanical components of these components. To this end, the controller 122 includes a computer program embodied on computer-readable media that is designed to run and while running, generate and forward commands to the various components, receive signals from the components and/or gather and store data relating to the operation of the components. The computer program can also performed any other control functions needed for use of the drive consoles 124, 126, syringe pump assemblies 128, 130 and sample collector 132.

FIG. 9 also shows fluid connections 134, 136 between the drive consoles 124, 126 and a respective associated one of the syringe pump assemblies 128, 130. These fluid connections extend from the vessels to the syringe pumps and are of the same type as depicted in FIGS. 6 and 7.

Using the controller 122, different test methods can be programmed into the controller 122, with possible variables being adjusted between the different test methods including the sampling time interval, the sampling volume, etc. Controller 122 therefore can run multiple and different methods and each method can be run in parallel independent of the others, e.g., drive console 124 and syringe pump assembly 128 can be controlled to perform one test method while drive console 126 and syringe pump assembly 130 can be controlled to simultaneously perform a second, different test method.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

The invention claimed is:

1. An arrangement for conducting transdermal diffusion cell testing, comprising:
   at least one vessel, each of said at least one vessel including a container defining an interior chamber having an opening at an upper end over which skin is placed, and a first inlet port and a first outlet port spaced apart from one another and each including a conduit communicating with said chamber, said first outlet port being arranged above said first inlet port and being arranged proximate said opening at said upper end of said chamber,
   a solution source fluidly coupled to each of said at least one vessel;
   a waste receptacle fluidly coupled to each of said at least one vessel;
   at least one syringe pump fluidly coupled to a respective one of said at least one vessel; and
   a sample collector fluidly coupled to said at least one syringe pump;
   said at least one syringe pump being controlled to provide a first flow path of solution from said solution source to said waste receptacle through said at least one vessel in order to fill said chamber with solution and being controlled to provide a second flow path of solution from said chamber to said sample collector,
   said at least one syringe pump being further controlled to take a sample from said chamber in the respective one of said at least one vessel before an actual sampling time to pre-condition a syringe of said at least one syringe pump.

2. The arrangement of claim 1, further comprising a tilting mechanism that positions said at least one vessel into a horizontal condition while said at least one syringe pump is controlled to provide the first flow path and into a tilted condition when said at least one syringe pump is controlled to provide the second flow path.

3. The arrangement of claim 1, wherein said at least one syringe pump includes a syringe oriented with its syringe inlet facing downward and its plunger vertically movable upward and downward.

4. The arrangement of claim 1, further comprising a controller that controls said at least one syringe pump.

5. The arrangement of claim 1, wherein in each of said at least one vessel, said first outlet port is angled at an angle of from about 20° to about 30° downward relative to an upper surface of said container.

6. The arrangement of claim 1, wherein each of said at least one vessel further includes a casing arranged at least partially around and spaced apart from at least a portion of said container to thereby define a compartment therebetween which is not in flow communication with said chamber, and a second inlet port and a second outlet port spaced apart from one another and each including a conduit communicating with said compartment.

7. The arrangement of claim 6, further comprising a fluid circulating mechanism that circulates fluid through said compartment via said second inlet and outlet ports.

8. An arrangement for conducting transdermal diffusion cell testing, comprising:
   at least one vessel, each of said at least one vessel including a container defining an interior chamber having an opening at an upper end over which skin is placed, and a first inlet port and a first outlet port spaced apart from one another and each including a conduit communicating with said chamber, said first outlet port being arranged above said first inlet port and being arranged proximate said opening at said upper end of said chamber,
   a solution source fluidly coupled to each of said at least one vessel;
   a waste receptacle fluidly coupled to each of said at least one vessel;
   at least one syringe pump fluidly coupled to a respective one of said at least one vessel; and
   a sample collector fluidly coupled to said at least one syringe pump;
   said at least one syringe pump being controlled to provide a first flow path of solution from said solution source to said waste receptacle through said at least one vessel in order to fill said chamber with solution and being controlled to provide a second flow path of solution from said chamber to said sample collector,
   said at least one syringe pump and said sample collector being controlled to pass solution to wash a fluid conduit between said at least one syringe pump and said sample collector immediately prior to conducting sampling.

9. The arrangement of claim 8, further comprising a controller that controls said at least one syringe pump and said sample collector.

10. The arrangement of claim 8, further comprising a tilting mechanism that positions said at least one vessel into a horizontal condition while said at least one syringe pump is controlled to provide the first flow path and into a tilted condition when said at least one syringe pump is controlled to provide the second flow path.

11. The arrangement of claim 8, wherein said at least one syringe pump includes a syringe oriented with its syringe inlet facing downward and its plunger vertically movable upward and downward.

12. The arrangement of claim 8, wherein in each of said at least one vessel, said first outlet port is angled at an angle of from about 20° to about 30° downward relative to an upper surface of said container.

13. The arrangement of claim 8, wherein each of said at least one vessel further includes a casing arranged at least partially around and spaced apart from at least a portion of said container to thereby define a compartment therebetween which is not in flow communication with said chamber, and a second inlet port and a second outlet port spaced apart from one another and each including a conduit communicating with said compartment.

14. The arrangement of claim 13, further comprising a fluid circulating mechanism that circulates fluid through said compartment via said second inlet and outlet ports.

15. An arrangement for conducting transdermal diffusion cell testing, comprising:
   at least one vessel, each of said at least one vessel including a container defining an interior chamber having an opening at an upper end over which skin is placed, and a first inlet port and a first outlet port spaced apart from one another and each including a conduit communicating with said chamber, said first outlet port being arranged above said first inlet port and being arranged proximate said opening at said upper end of said chamber,
   a solution source fluidly coupled to each of said at least one vessel;
   a waste receptacle fluidly coupled to each of said at least one vessel;
   at least one syringe pump fluidly coupled to a respective one of said at least one vessel; and
   a sample collector fluidly coupled to said at least one syringe pump;
   said at least one syringe pump being controlled to provide a first flow path of solution from said solution source to said waste receptacle through said at least one vessel in order to fill said chamber with solution and being controlled to provide a second flow path of solution from said chamber to said sample collector, said at least one syringe pump being further controlled to draw solution from a fluid conduit between said at least one syringe pump and said sample collector after sampling is completed and direct the drawn solution to said chamber in the respective one of said at least one vessel.

16. The arrangement of claim 15, further comprising a controller that controls said at least one syringe pump.

17. The arrangement of claim 15, further comprising a tilting mechanism that positions said at least one vessel into a horizontal condition while said at least one syringe pump is controlled to provide the first flow path and into a tilted condition when said at least one syringe pump is controlled to provide the second flow path.

18. The arrangement of claim 15, wherein said at least one syringe pump includes a syringe oriented with its syringe inlet facing downward and its plunger vertically movable upward and downward.

19. The arrangement of claim 15, wherein each of said at least one vessel further includes a casing arranged at least partially around and spaced apart from at least a portion of said container to thereby define a compartment therebetween which is not in flow communication with said chamber, and a second inlet port and a second outlet port spaced apart from one another and each including a conduit communicating with said compartment.

20. The arrangement of claim 19, further comprising a fluid circulating mechanism that circulates fluid through said compartment via said second inlet and outlet ports.

* * * * *